(12) United States Patent
Aya et al.

(10) Patent No.: US 10,052,261 B1
(45) Date of Patent: Aug. 21, 2018

(54) MEDICATION AND MEDICAL SUPPLY DISPENSER

(71) Applicant: SIMEKS TIBBI SISTEMLER SANAYI VE TICARET A.S., Istanbul (TR)

(72) Inventors: Hakan Seber Aya, Istanbul (TR); Bahar Sunman, Istanbul (TR); Gercek Sunman, Istanbul (TR)

(73) Assignee: SIMEKS TIBBI SISTEMLER SANAYI VE TICARET A.S., Istanbul (TR)

( * ) Notice: Subject to any disclaimer, the term of this patent is extended or adjusted under 35 U.S.C. 154(b) by 0 days.

(21) Appl. No.: 15/746,427

(22) PCT Filed: Jul. 14, 2016

(86) PCT No.: PCT/EP2016/066773
§ 371 (c)(1),
(2) Date: Jan. 22, 2018

(87) PCT Pub. No.: WO2017/012983
PCT Pub. Date: Jan. 26, 2017

(30) Foreign Application Priority Data

Jul. 22, 2015 (EP) .................. 15177861

(51) Int. Cl.
*G07F 11/62* (2006.01)
*A61J 7/04* (2006.01)
*G07F 17/00* (2006.01)

(52) U.S. Cl.
CPC .......... *A61J 7/0481* (2013.01); *A61J 7/0454* (2015.05); *G07F 11/62* (2013.01); *G07F 17/0092* (2013.01)

(58) Field of Classification Search
CPC ....... G07F 17/0092; G07F 11/62; G07F 11/18
(Continued)

(56) References Cited

U.S. PATENT DOCUMENTS

| | | | | |
|---|---|---|---|---|
| 6,994,409 B2* | 2/2006 | Godlewski | ............. | A47B 63/06 312/215 |
| 7,146,247 B2* | 12/2006 | Kirsch | .................... | G07F 9/026 700/236 |

(Continued)

FOREIGN PATENT DOCUMENTS

| | | |
|---|---|---|
| CA | 2311269 A1 | 12/2001 |
| JP | 2002293414 A | 10/2002 |
| WO | 9826746 A2 | 6/1998 |

*Primary Examiner* — Timothy R Waggoner
(74) *Attorney, Agent, or Firm* — Gokalp Bayramoglu

(57) ABSTRACT

A medication and medical supply dispenser system (100) comprising a substantially planar base (1), a plurality of separators (2) for being removably fixed on the base and thus for defining separated compartments (3) thereon, said system being connectable to a further device having computing and data storage abilities wherein the system further comprises or is cooperable with a set (50) of aligned transducers, each separator is provided with a counterpart, proximity of said counterpart being detectable by any of said transducers; such that in use, when the system is connected to said further device, and the base is scanned by the set, a matrix of relative positions of any separators fixed on the base is generated, and thus a map of separated compartments is generated for preparation of rules for authorization-based selective access to a certain compartment.

13 Claims, 5 Drawing Sheets

(58) Field of Classification Search
USPC .................................................. 700/231–244
See application file for complete search history.

(56) References Cited

U.S. PATENT DOCUMENTS

| | | | |
|---|---|---|---|
| 7,630,791 B2* | 12/2009 | Nguyen | ............... A61G 12/001 |
| | | | 700/236 |
| 8,588,966 B2* | 11/2013 | Michael | ................ A61J 7/0084 |
| | | | 221/122 |
| 8,794,482 B2 | 8/2014 | Sack et al. | |
| 2004/0031574 A1* | 2/2004 | Gambarelli | ............. B65G 1/02 |
| | | | 160/122 |
| 2007/0135965 A1 | 6/2007 | Nguyen et al. | |
| 2008/0065264 A1* | 3/2008 | Omura | ................ G06Q 10/087 |
| | | | 700/231 |
| 2008/0264967 A1* | 10/2008 | Schifman | ................ G07F 11/44 |
| | | | 221/133 |
| 2009/0198347 A1* | 8/2009 | Kirzinger | ................ G07F 11/62 |
| | | | 700/1 |
| 2012/0004764 A1 | 1/2012 | Rahilly et al. | |
| 2014/0311942 A1 | 10/2014 | Flynn | |

* cited by examiner

MEDICATION AND MEDICAL SUPPLY DISPENSER

CROSS REFERENCE TO RELATED APPLICATIONS

This application is the national phase entry of International Application No. PCT/EP2016/066773, filed on Jul. 14, 2016, which claims priority from the EP application no. 15177861.0 filed on Jul. 22, 2015, the entire contents of which are incorporated herein by reference.

TECHNICAL FIELD

The present invention relates to a system for storage and distribution of medications and medical supplies.

BACKGROUND

Medication and medical supply dispensers are medicament and medical supply storage and distribution boxes with a plurality of compartments, and they are generally used for providing pre-planned time-based distribution of dosage forms. Usually, a dispenser is filled with medications and medical supply by an authorized person in accordance with predetermined stock levels, and sealed for timely access by respective care giver, in accordance with respective treatment plans. A treatment plan may comprise administration of different medicaments in variable amounts throughout the treatment. Such variable amounts may result in variation of volume in daily dosages.

A pill dispenser with a uniform compartment volume (as in CA 2 311 269 A1, US 2014 311 942 A1, U.S. Pat. No. 8,794,482 B2 etc.) has a drawback that the volume of a compartment may not fit to a volume of a daily dose and/or stock level. If the medicaments volume varies such that one or more days throughout the treatment plan require high amounts of compartment volume, respective daily doses may not fit into a compartment. Or if the compartments are large enough to receive high volumes of daily doses, some of the compartment volumes may not be able to be used efficiently in case where the treatment plan comprises low-dose days requiring low volume compartments.

Lack of flexibility in time-based distribution of medicaments in accordance with treatment plans comprising variable daily doses, using a medication dispenser, is an important issue to overcome.

SUMMARY

Primary object of the present invention is to overcome the shortcomings in the prior art.

Another object of the present invention is to provide a medication and medical supply dispenser system, compartment sizes of which can be pre-arranged flexibly in accordance with requirements of different treatment plans and/or stock levels.

Another object of the present invention is to provide a medication and medical supply dispenser with effective use of volume.

Another object of the present invention is to provide a medication and medical supply dispenser with high precision by allowing access to respective compartments thereof.

Another object of the present invention is to provide a method of pre-planned distribution of dosage forms.

A medication and medical supply dispenser system comprising a substantially planar base, a plurality of separators for being removably fixed on the base and thus for defining separated compartments thereon, said system being connectable to a further device having computing and data storage abilities wherein the system further comprises or is cooperable with a set of aligned transducers, each separator is provided with a counterpart, proximity of said counterpart being detectable by any of said transducers; such that in use, when the system is connected to said further device, and the base is scanned by the set, a matrix of relative positions of any separators fixed on the base is generated, and thus a map of separated compartments is generated for preparation of rules for authorization-based selective access to a certain compartment.

BRIEF DESCRIPTION OF THE DRAWINGS

The figures whose brief explanations are herewith provided are solely intended for providing a better understanding of the present invention and are as such not intended to define the scope of protection or the context in which said scope is to be interpreted in the absence of the description.

DETAILED DESCRIPTION OF THE INVENTION

Figure 1:
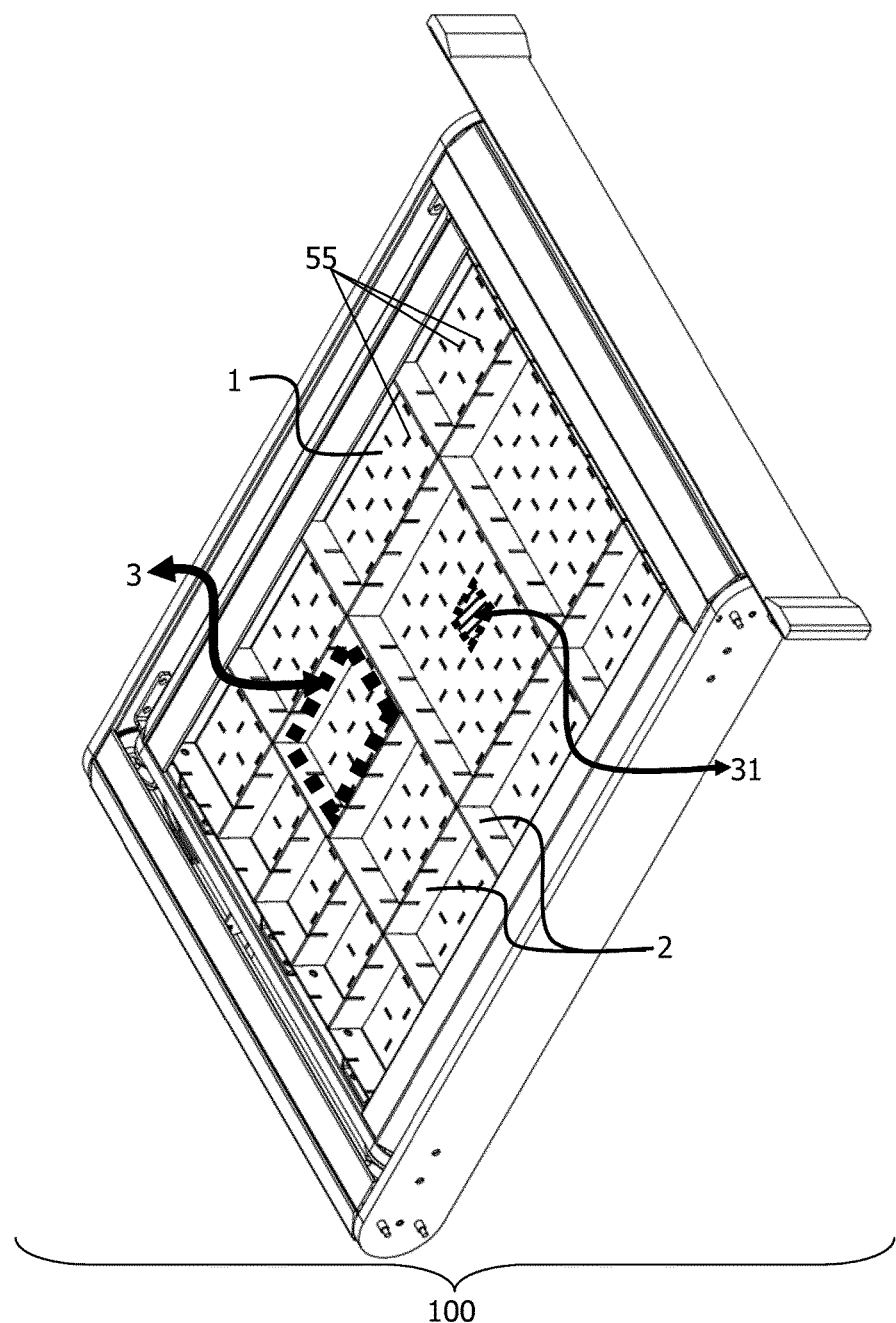
FIG. 1 represents a perspective view of the system according to the present invention, wherein the base is provided with several compartments of various sizes, wherein all of the compartments are fully available for access.

Referring now the figures outlined above, the present invention proposes a medication and medical supply dispenser system. As exemplified in FIG. 1, the system (100) comprises a substantially planar base (1), a plurality of separators (2) for being removably fixed on the base and thus for defining separated compartments (3) (one example for the compartments is shown with bold dashed polygon on FIG. 1) thereon, said system being connectable to a further device (not shown) having computing and data storage abilities, wherein the system further comprises or is cooperable with a set (50) of aligned transducers (not shown), each separator is provided with a counterpart (not shown), position of which being detectable by any of said transducers;

such that in use, when the system is connected to said further device, and the base is scanned by the set, a matrix of relative positions of any separators fixed on the base is generated, and thus a map of separated compartments is generated for preparing rules for authorization-based selective access to a certain compartment.

The system of the present invention enables flexible arrangement of compartment sizes for receiving various size daily doses and/or stock levels of e.g. dosage forms to be administrated to a patient. Once the compartments (3) of pre-planned required sizes are defined by placing the separators (2) onto the base (1), digital mapping of the compartments can be achieved by scanning the base (preferably in full extent of the base footprint) by the set (50) (which may be e.g. a strip-shaped sensor) which comprises a plurality of aligned transducers (not shown). As the base gets scanned by moving the set thereon, sensor data is transferred and logged on the further device having computing abilities. Sensor data here is preferably a time- and velocity-based coordinate information on counterparts detected by any transducer of the set (50). Coordinate information of counterparts (not shown) correspond to coordinate information of separators, and thus spaces between separators can be determined by determination of said coordinate information. Distances between successive separators correspond to width or length of respective compartments adjacent to respective separators. Multiplication between respective widths and lengths correspond to compartment base areas (i.e. compartment footprints).

In a preferred embodiment according to the present invention, the transducers are Hall Effect sensors, and accordingly, the counterparts are magnetic. This enables position detection (i.e. locating of separators) by proximity detection of the counterparts even when the set scans throughout the base without mechanically contacting the counterparts, thanks to the magnetic interaction between Hall Effect sensors and the magnetic counterparts.

Figure 2:
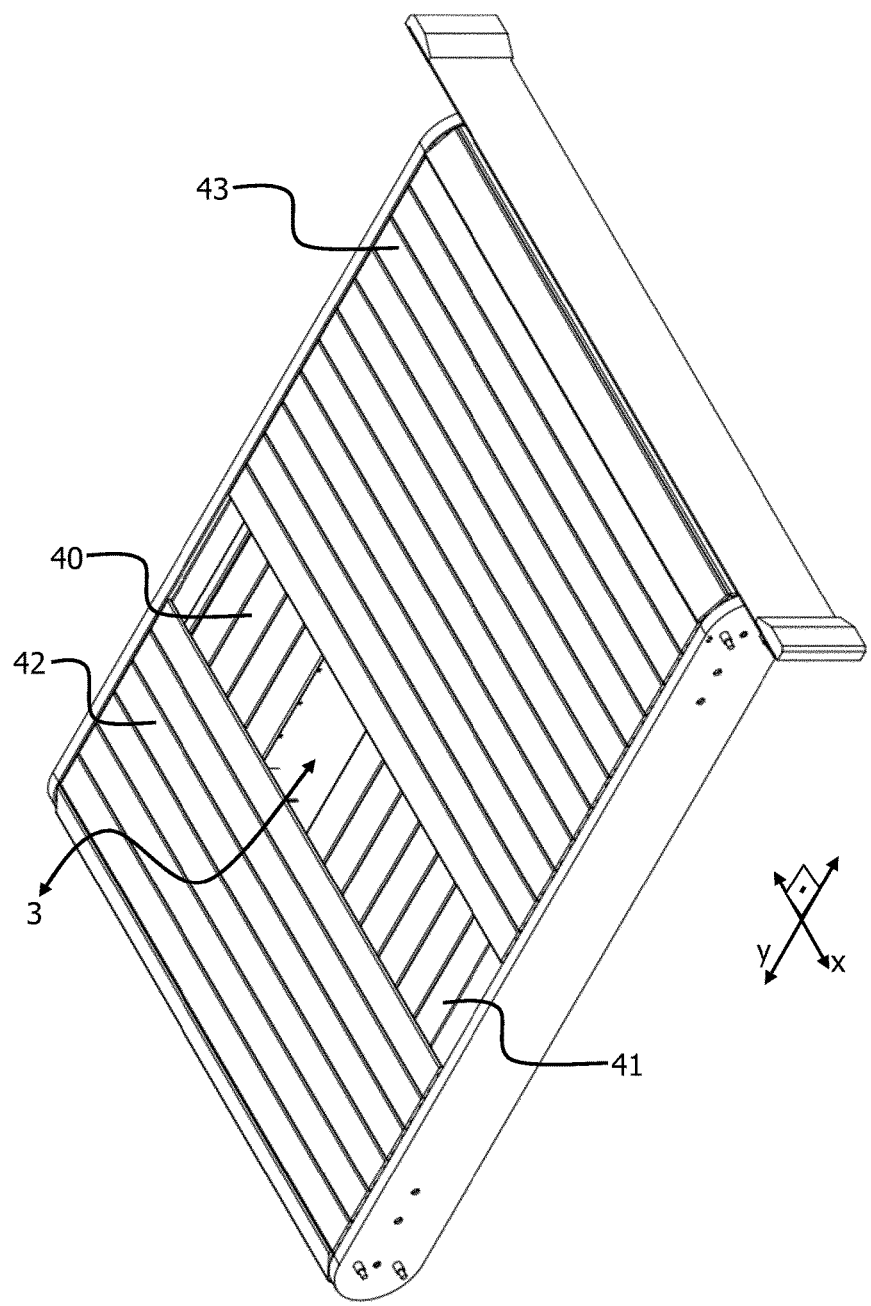
FIG. 2 represents a perspective view of the system according to the present invention, wherein only one compartment is available for access and the rest of the compartments are covered by sliding covers.
Figure 3:
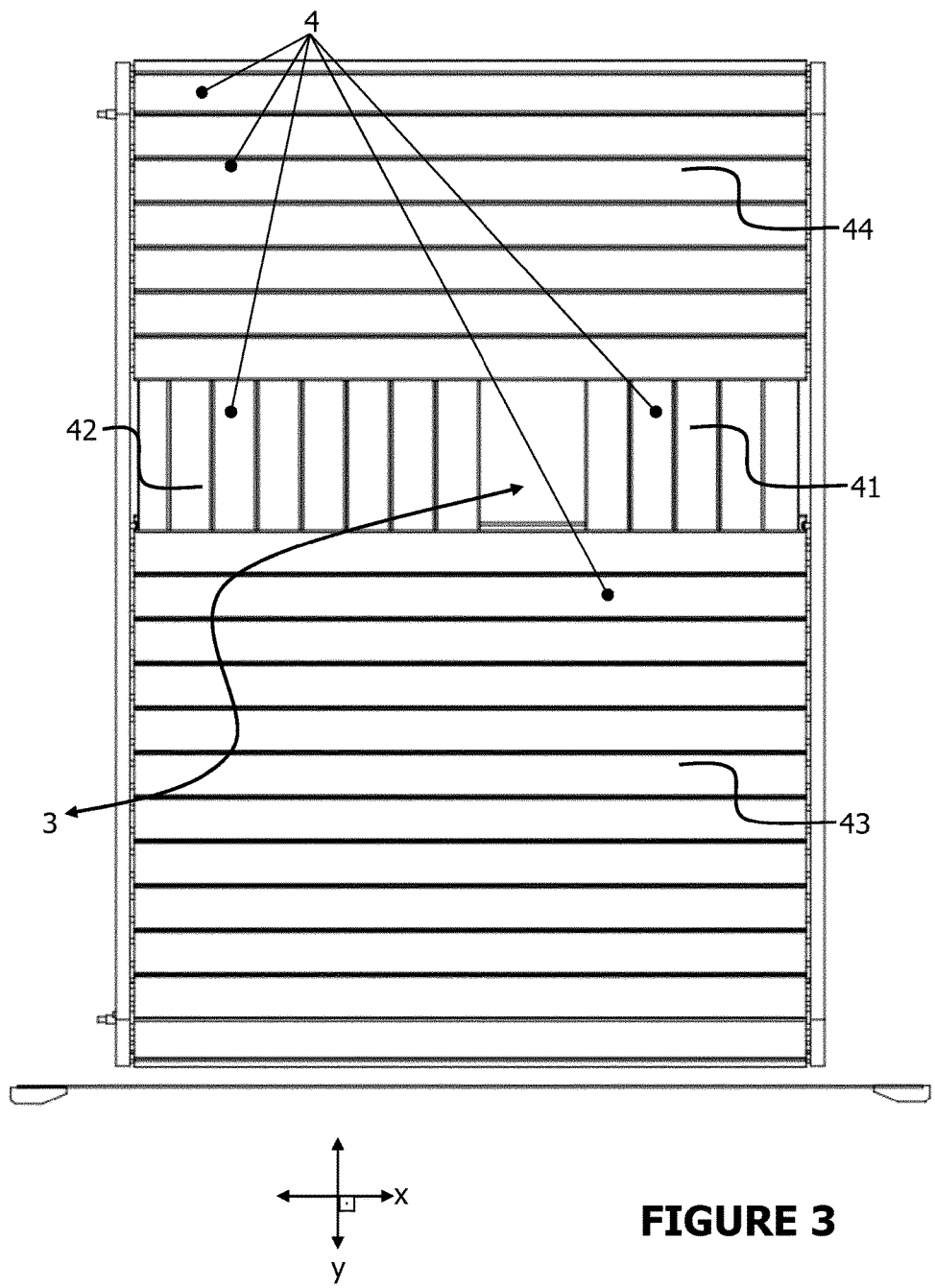
FIG. 3 represents a plan view of the system shown in FIG. 2, wherein only one compartment is available for access and the rest of the compartments are covered by sliding covers.

In an embodiment according to the present invention, exemplified in FIG. 2 and FIG. 3, the system is provided with a first set of sliding covers (40 and 41) movable on a first linear axis (shown as x-axis on FIG. 2) parallel to the base, and a second set of sliding covers (42 and 43) movable on a second linear axis (shown as y-axis on FIG. 2) parallel to the base and perpendicular to said first linear axis; for partly or fully covering the base thus for providing or limiting access to the compartments. In this embodiment, the system further comprises motors dedicated to each sliding cover for rolling and unrolling them. Thus, the rules for authorization-based selective access to a certain compartment can be implemented by provision or limiting access thereto.

In an embodiment according to the present invention, the set is located on a sliding cover. In a preferred embodiment, the sliding covers are mainly built of slides (4), and one of the slides of a sliding cover (41, 42, 43 or 44) is provided with the set. In this case, the scanning can be performed through a from side to side movement of said slide throughout the base.

Figure 4:
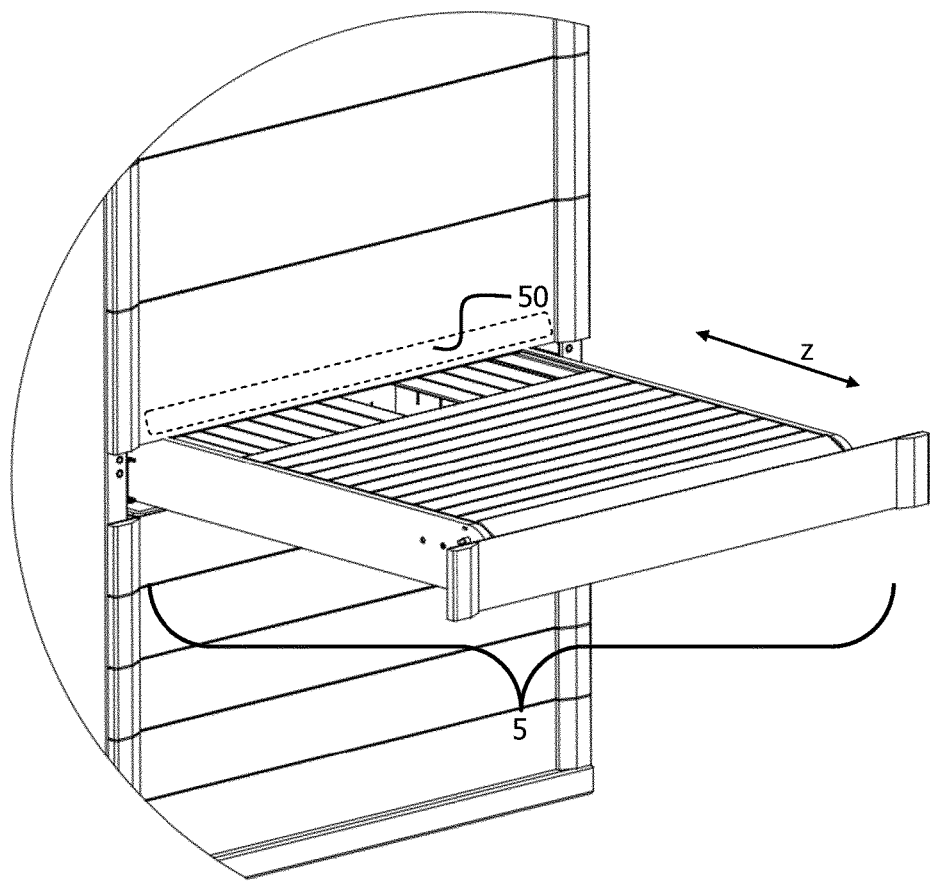
FIG. 4 exemplifies a use of the system according to the present invention in a drawer or as one, wherein a slide of a sliding cover is provided with the set.
Figure 5:
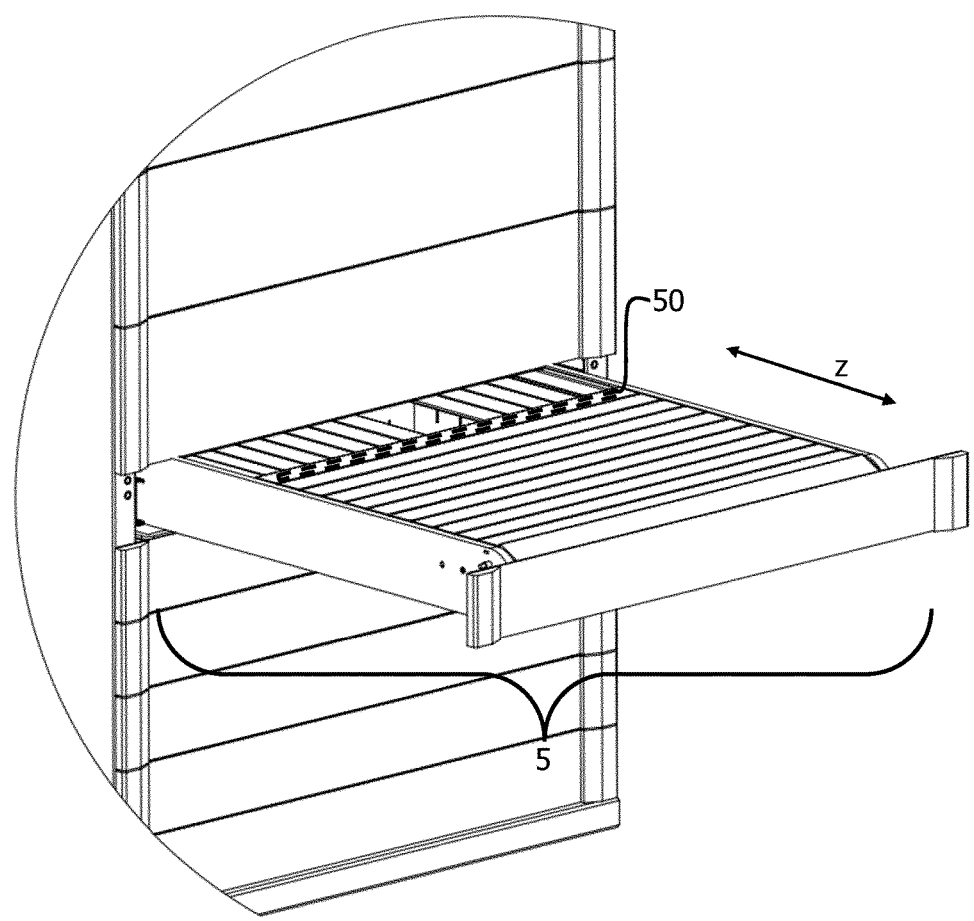
FIG. 5 exemplifies a use of the system according to the present invention in a drawer or as one, wherein the set is located in proximity of an opening on a surface perpendicular to the movement axis of the base (z-axis).

In an alternative embodiment according to the present invention, exemplified in FIG. 4, the base is linearly movable on a drawer (5) which can be either manually driven or motor-driven through an opening on a surface perpendicular to the movement axis (shown as z-axis) of the base (e.g. the base is such drawer itself, or the base can be put into such drawer), and the set (50) (symbolically shown as a dashed bar) is located in proximity of the opening such that the scanning of the base by the set is performed during motion of the drawer through the opening. In this case, the scanning can be performed via a full movement of the drawer through the opening, in a direction on said axis.

In a preferred embodiment according to the present invention, the base comprises a series of reference magnets located
    along the direction of sliding of the sliding covers in case where the set is located on a sliding cover, or
    along the direction of the linear motion of the drawer in case where the base is linearly movable on a drawer;
and the scanning of the base by the set is performed by sliding of the base and set relative to each other. This provides formation of the matrix, independently from the velocity of the sliding cover or from the velocity of the drawer motion.

In an alternative embodiment according to the present invention, the scanning of the base by the set is performed by sliding of the base and set relative to each other with a uniform speed. This provides formation of a distance-based matrix of counterpart coordinates by using such speed.

In a preferred embodiment according to the present invention, a minimum compartment footprint (31) (size of the area demonstrated with an exemplary shaded region on FIG. 1) is defined as an aliquot of total footprint area of the base (i.e. sum of all compartment footprint areas available on the base); and the base is provided with guides (55) for matching with separators such that compartment sizes can only be arranged to be multiples of said minimum compartment footprint. Here, basically, a minimum compartment footprint (size) is defined as an aliquot of total available footprint (size) of the base. Furthermore, minimum compartment size (or footprint) is in accordance with edge lengths of a compartment having the minimum footprint. In case that the minimum footprint is mainly in shape of square, the edge lengths of said square can be considered as minimum edge length. Designation of minimum compartment footprints (in other words, minimum compartment areas which are not further dividable by guides for separators) using guides (55) for separators serves for accurate detection of scanning and precise mapping of compartments, since minimum available distance between two guides on the base, which are parallel to each other can preferably be selected in accordance with the detection resolution of the set which may correspond to distances between the aligned transducers.

In an embodiment according to the present invention, each motor is step motor. Preferably, step lengths of the motors are arranged such that each step of a motor corresponds to the minimum edge length (i.e. the minimum available distance between two guides on the base, which are parallel to each other). With this embodiment, enhanced precision on access to the compartments is achieved. The step length is preferably smaller than the range of the transducer, said range corresponding to the maximum distance between a transducer and a counterpart wherein detection of the counterpart by the transducer is possible. In this case, the step length is preferably smaller than the half of the transducer range, more preferably smaller than one tenth of the transducer range, even more preferably smaller than one tenth of the transducer range. In such case, precise alignment of the set on a certain separator is available and further enhanced precision on access to the compartments is achieved; especially if Hall Effect sensors are used as transducers in the set.

The present invention further provides a method of pre-planning of distribution of dosage forms in accordance with time-based treatment plans and/or stock levels.

The method comprises following sequential steps:
    a) determination of a time-based distribution plan for distribution of dosage forms in accordance with a respective treatment plan for a patient,
    b) determination of required compartment sizes for receiving respective time-based amounts (e.g. daily amounts) of said dosage forms to be distributed,
    c) dividing the base of a pill dispenser system having a substantially planar base by removably fixing a plurality of separators thereon, thus defining separated compartments on the base, said compartments having variable sizes in accordance with required compartment sizes for receiving variable respective time-based amounts of the dosage forms; said separators being provided with counterparts detectable by a set of aligned transducers;

and then optionally loading said time-based amounts into respective compartments, d) scanning the base by the set whilst the system is connected to a further device having computing and data storage abilities, by that way generation a matrix of relative positions of any separators fixed on the base, e) generation of a map of separated compartments for preparing rules for authorization-based selective access to a certain compartment.

The method preferably further comprises moving a first set of sliding covers movable on a first linear axis parallel to the base, and moving a second set of sliding covers movable on a second linear axis parallel to the base and perpendicular to said first linear axis;

thus selectively partly or fully covering said base thus providing or limiting access to the compartments; such that only a certain compartment which is pre-determined by an authorized person for being accessible is fully accessible on the pre-determined time for administration of the time-based dosage from the accessible compartment; and such that rest of the compartments which are pre-determined to be inaccessible on said time, being inaccessible by an unauthorized person.

Following objects are achieved by the present invention:
overcoming the shortcomings in the prior art,
provision of a medication and medical supply dispenser system, compartment sizes of which can be pre-arranged flexibly in accordance with requirements of different treatment plans and/or stock levels,
provision of a pill dispenser with effective use of volume,
provision of a pill dispenser with high precision by allowing access to respective compartments thereof,
provision of a method for pre-planned distribution of dosage forms.

The invention claimed is:

1. A medication and medical supply dispenser system comprising a substantially planar base, a plurality of separators for being removably fixed on the base for defining separated compartments thereon, wherein the medication and medical supply dispenser system is connectable to a computing and data storage device,
the medication and medical supply dispenser system further comprises a set of aligned transducers,
each separator is provided with a counterpart, wherein a position of the counterpart is detectable by any of said transducers;
wherein the transducers are Hall Effect sensors and the counterparts are magnetic; wherein a scanning of the base is performed with a relative movement of the set of aligned transducers on the base with a uniform speed.

2. The medication and medical supply dispenser system according to the claim 1, wherein the medication and medical supply dispenser system further comprises a first set of sliding covers movable on a first linear axis parallel to the base, and a second set of sliding covers movable on a second linear axis parallel to the base and perpendicular to the first linear axis; wherein the first set of sliding covers and the second set of sliding covers partly or fully cover the base providing or limiting an access to the compartments; the medication and medical supply dispenser system further comprises a plurality of motors for rolling and unrolling the first set of sliding covers and the second set of sliding covers.

3. The medication and medical supply dispenser system according to the claim 2, wherein the set of aligned transducers is located on a sliding cover.

4. The medication and medical supply dispenser system according to the claim 3, wherein the base comprises a series of reference magnets located along the direction of sliding of the sliding covers.

5. The medication and medical supply dispenser system according to the claim 2, wherein each motor is a step motor, having a step length smaller than a range of the transducer, the range corresponding to a maximum distance between the transducer and the counterpart suitable for detection of the counterpart by the transducer.

6. The medication and medical supply dispenser system according to the claim 2, wherein the sliding covers include slides, and a slide of the sliding cover is provided with the set of aligned transducers.

7. The medication and medical supply dispenser system according to the claim 2, wherein the base is linearly movable on a drawer through an opening on a surface perpendicular to the movement axis of the base, and the set of aligned transducers is located in proximity of the opening such that the scanning of the base by the set of aligned transducers is performed during motion of the drawer through the opening.

8. The medication and medical supply dispenser system according to the claim 7, wherein the base comprises a series of reference magnets located along the direction of the linear motion of the drawer.

9. The medication and medical supply dispenser system according to the claim 1, wherein a minimum compartment footprint is defined as an aliquot of total footprint area of the base; and wherein the base is provided with guides for matching with separators such that compartment sizes can only be arranged to be multiples of minimum compartment footprint.

10. The medication and medical supply dispenser system according to the claim 1, wherein the computing and data storage device is integrated within the medication and medical supply dispenser system.

11. A method of pre-planning of distribution of dosage forms in accordance with time-based treatment plans and/or stock levels, where a time-based distribution plan for distribution of dosage forms in accordance with a respective treatment is determined for a patient; and where required compartment sizes for receiving respective time-based amounts of said dosage forms to be distributed are determined; the method comprising the sequential steps of:

a) dividing the base of a medication and medical supply dispenser system having a substantially planar base by removably fixing a plurality of separators thereon, thus defining separated compartments on the base, the compartments having variable sizes in accordance with required compartment sizes for receiving variable respective time-based amounts of the dosage forms; the separators being provided with magnetic counterparts detectable by a set of aligned transducers which are Hall Effect sensors;

and then optionally loading said time-based amounts into respective compartments, b) scanning the base by the set of aligned transducers whilst the system is connected to a computing and data storage device and generating a matrix of relative positions of any separators fixed on the base, wherein scanning of the base is performed with a relative movement of the set of aligned transducers on the base with a uniform speed, c) generating a map of separated compartments for preparing rules for authorization-based selective access to a certain compartment.

12. The method according to the claim 11, wherein the base comprises a series of reference magnets located along the direction of sliding of the sliding covers in case where the set of aligned transducers is located on a sliding cover, or along the direction of the linear motion of the drawer in case where the base is linearly movable on a drawer;

and the scanning of the base by the set of aligned transducers is performed by sliding of the base and the set of aligned transducers relative to each other.

13. The method according to the claim 11, further comprising moving a first set of sliding covers movable on a first linear axis parallel to the base, and moving a second set of sliding covers movable on a second linear axis parallel to the base and perpendicular to said first linear axis; thus selectively partly or fully covering said base thus providing or limiting access to the compartments; such that only a certain compartment which is pre-determined by an authorized person for being accessible is fully accessible for administration of the time-based dosage from the accessible compartment; and such that rest of the compartments which are pre-determined to be inaccessible, being inaccessible by an unauthorized person.

* * * * *